(12) United States Patent
Bartosch et al.

(10) Patent No.: US 10,111,686 B2
(45) Date of Patent: Oct. 30, 2018

(54) DEVICE FOR THE TRANSCUTANEOUS IMPLANTATION OF EPICARDIAL PACEMAKER ELECTRODES

(71) Applicant: DEUTSCHES HERZZENTRUM BERLIN, Berlin (DE)

(72) Inventors: Marco Bartosch, Berlin (DE); Heiner Peters, Berlin (DE); Boris Schmitt, Berlin (DE); Björn Peters, Berlin (DE)

(73) Assignee: DEUTSCHES HERZZENTRUM BERLIN, Berlin (DE)

( * ) Notice: Subject to any disclaimer, the term of this patent is extended or adjusted under 35 U.S.C. 154(b) by 151 days.

(21) Appl. No.: 15/100,249

(22) PCT Filed: Nov. 27, 2014

(86) PCT No.: PCT/EP2014/075821
§ 371 (c)(1),
(2) Date: May 27, 2016

(87) PCT Pub. No.: WO2015/078971
PCT Pub. Date: Jun. 4, 2015

(65) Prior Publication Data
US 2017/0000523 A1    Jan. 5, 2017

(30) Foreign Application Priority Data

Nov. 27, 2013 (DE) .......................... 10 2013 224 283

(51) Int. Cl.
*A61B 19/00* (2006.01)
*A61B 17/34* (2006.01)
(Continued)

(52) U.S. Cl.
CPC .......... *A61B 17/3468* (2013.01); *A61B 90/11* (2016.02); *A61N 1/0587* (2013.01); *A61B 2017/00871* (2013.01)

(58) Field of Classification Search
CPC ... A61N 1/0587; A61B 90/11; A61B 17/3468; A61B 2017/00871
See application file for complete search history.

(56) References Cited

U.S. PATENT DOCUMENTS 5,871,532 A     2/1999 Schroeppel
7,369,901 B1 *  5/2008 Morgan ................. A61N 1/059
                                                        600/375
(Continued)

FOREIGN PATENT DOCUMENTS

DE    29909082 U1    7/1999
DE    60303570 T2    9/2006
(Continued)

OTHER PUBLICATIONS

Abraham, W.T. et al., Devices in the management of advanced, chronic heart failure, Nature Reviews Cardiology 10, 98-110, Feb. 2013.
(Continued)

*Primary Examiner* — Son Dang
(74) *Attorney, Agent, or Firm* — Maschoff Brennan

(57) ABSTRACT

It is provided a device for the transcutaneous implantation of an epicardial pacemaker electrode, which is arranged in a tubular, flexible implantation catheter insertable into the pericardial space. The distal end area of the electrode is connected to a shape-variable element for aligning the electrode, in particular for adjusting the implantation angle thereof, and for stabilizing, in particular laterally stabilizing, the electrode.

9 Claims, 10 Drawing Sheets

(51) Int. Cl.
*A61N 1/05* (2006.01)
*A61B 90/11* (2016.01)
*A61B 17/00* (2006.01)

(56) References Cited

U.S. PATENT DOCUMENTS

| | | | |
|---|---|---|---|
| 7,930,040 B1 | 4/2011 | Kelsch et al. | |
| 7,991,484 B1 | 8/2011 | Sengupta et al. | |
| 8,062,315 B2* | 11/2011 | Aster | A61B 17/3421 606/153 |
| 8,216,302 B2* | 7/2012 | Wilson | A61F 2/2427 623/2.11 |
| 9,539,423 B2* | 1/2017 | Bonner | A61N 1/0592 |
| 2003/0158575 A1 | 8/2003 | Boylan et al. | |
| 2005/0004644 A1* | 1/2005 | Kelsch | A61B 17/8888 607/131 |
| 2005/0065591 A1* | 3/2005 | Moberg | A61F 2/95 623/1.11 |
| 2005/0113822 A1 | 5/2005 | Fuimaono et al. | |
| 2005/0182465 A1 | 8/2005 | Ness | |
| 2007/0093890 A1* | 4/2007 | Eliasen | A61F 2/246 623/2.11 |
| 2007/0233200 A1 | 10/2007 | Maschke | |
| 2007/0255399 A1* | 11/2007 | Eliasen | A61F 2/246 623/2.36 |
| 2007/0265700 A1* | 11/2007 | Eliasen | A61F 2/246 623/2.1 |
| 2008/0288061 A1* | 11/2008 | Maurer | A61F 2/246 623/2.36 |
| 2009/0131849 A1* | 5/2009 | Maurer | A61F 2/246 604/9 |
| 2009/0204170 A1* | 8/2009 | Hastings | A61N 1/0565 607/33 |
| 2009/0204216 A1* | 8/2009 | Biedermann | A61B 17/744 623/17.12 |
| 2010/0087725 A1 | 4/2010 | Friedman et al. | |
| 2010/0324637 A1* | 12/2010 | Trip | A61N 1/057 607/116 |
| 2011/0015715 A1 | 1/2011 | Ollivier | |
| 2013/0338763 A1* | 12/2013 | Rowe | A61F 2/2427 623/2.11 |
| 2014/0194776 A1* | 7/2014 | Gunday | A61B 17/3478 600/567 |
| 2017/0312029 A1* | 11/2017 | Schaer | A61B 18/1492 |

FOREIGN PATENT DOCUMENTS

| | | | |
|---|---|---|---|
| DE | 102006015013 A1 | 10/2007 | |
| DE | 60 2004 005 845 T2 | 12/2007 | |
| DE | 60223537 T2 | 9/2008 | |
| EP | 1 661 600 A1 | 5/2006 | |
| EP | 2 266 657 A1 | 12/2010 | |
| WO | 2004/045675 A2 | 6/2004 | |
| WO | 2006/116310 A2 | 11/2006 | |
| WO | 2007/013927 A1 | 2/2007 | |

OTHER PUBLICATIONS

Bernstein et al., Survey of Cardiac Pacing and Implanted Defibrillator Practice Patterns in the United States in 1997, PACE 2001; 24:842-855.

Ector et al., The World Survey of Cardiac Pacing and Implantable Cardioverter Defibrillators: Calendar Year 1997—Europe, PACE 2001; 24:863-868.

Greenspon et al, Trends in permanent pacemaker implantation in the United States from 1993 to 2009: increasing complexity of patients and procedures, Cardiology Faculty Papers. (2012). Paper 18. http://jdc.jefferson.edu/cardiologyfp/18.

Mond et al., The 11th World Survey of Cardiac Pacing and Implantable Cardioverter-Defibrillators: Calendar Year 2009—A World Society of Arrhythmia's Project, PACE 2011; 34:1013-1027.

Mond et al., The World Survey of Cardiac Pacing and Cardioverter Defibrillators: Calendar Year 2001, PACE 2004; 27:955-964.

Mond et al., The World Survey of Cardiac Pacing and Cardioverter-Defibrillators: Calendar Year 2005, PACE 2008; 31:1202-1212.

Mond et al., The World Survey of Cardiac Pacing and Cardioverter Defibrillators: Calendar Year 1997—Asian Pacific, Middle East, South America, and Canada, PACE 2001; 24:856-862.

Mond, The World Survey of Cardiac Pacing and Cardioverter Defibrillators: Calendar Year 1997, PACE 2001: 24:869-870.

Parsonnet et al., The 1989 World Survey of Cardiac Pacing., PACE 1991: 14: 2073-2076.

Andre D'Avila et al: "Pericardial Anatomy for the Interventional Electrophysiologist" vol. 14, No. 4, Apr. 1, 2003.

\* cited by examiner

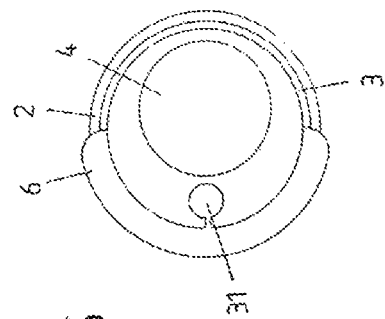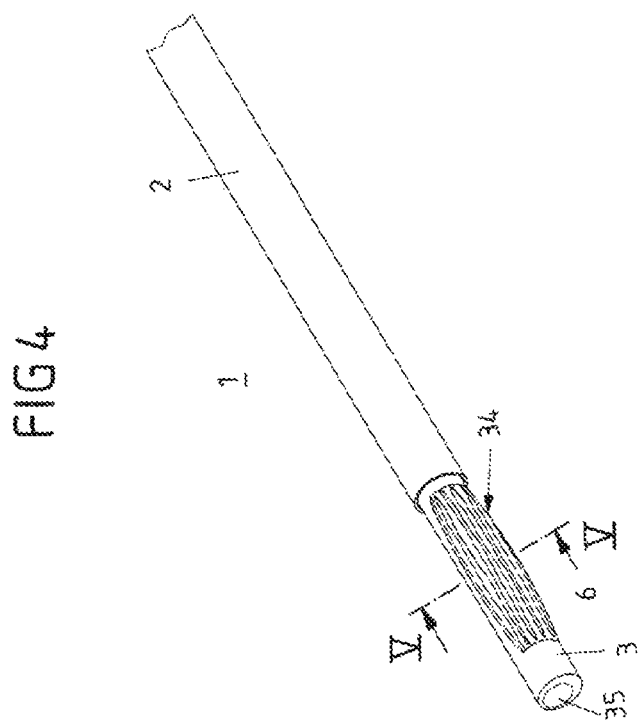

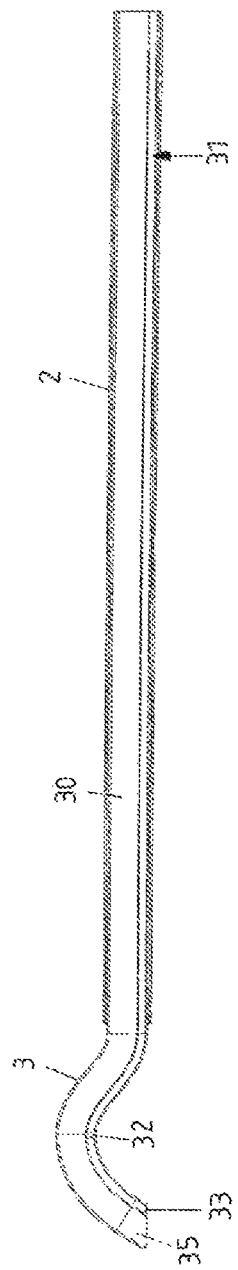

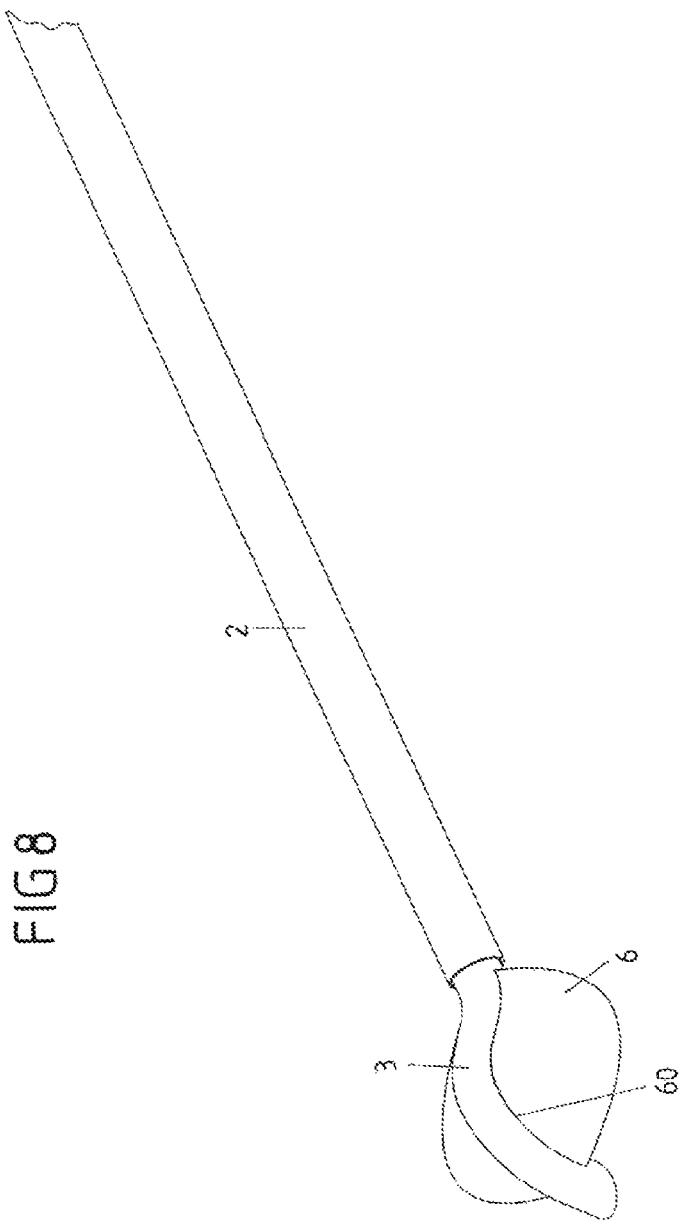

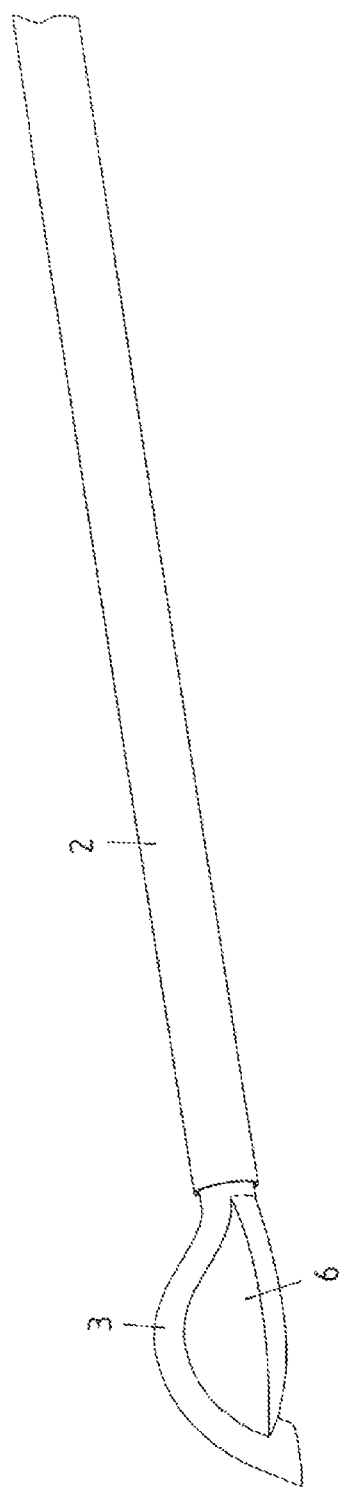

DEVICE FOR THE TRANSCUTANEOUS IMPLANTATION OF EPICARDIAL PACEMAKER ELECTRODES

CROSS-REFERENCE TO A RELATED APPLICATION

This application is a National Phase Patent Application of International Patent Application Number PCT/EP2014/075821, filed on Nov. 27, 2014, which claims priority of German Patent Application Number 10 2013 224 283.2, filed on Nov. 27, 2013.

BACKGROUND

The invention relates to a device for the transcutaneous implantation of an epicardial pacemaker electrode, which is arranged in a tubular, flexible implantation catheter insertable into the pericardial space.

After the pericardium has been punctured, an implantation catheter of this kind is introduced into the narrow, closed cavity formed between the epicardium and the parietal lamina of the pericardium, called the pericardial cavity or the pericardial space, and is advanced as far as the implantation site. At the implantation site, the epicardial pacemaker electrode, which is composed of an electrically insulated electrode line with one or more non-insulated distal contact points, is anchored in the epicardium/myocardium by means of an active fixing mechanism (e.g. a helix). The electrical impulses emitted from a pacemaker attached to the proximal end of the electrode can be transmitted to the myocardium via the electrode that has been thus fixed, and a controlled stimulation of the heart muscle is thereby triggered.

On account of the need to puncture the pericardium, and because of the very narrow pericardial space, the implantation catheter should have the smallest possible diameter in order to ensure a minimally invasive intervention, to minimize the danger of injury to surrounding organs or organ parts (e.g. pleura, diaphragm, myocardium or coronary vessels) and to permit sufficient spatial manipulation.

EP 2 266 657 A1 discloses an implantable electrode probe with a tubular, flexible probe body, an electrode arranged at the distal end of the probe body, and an electrical supply line guided in the probe body and leading to the electrode, in which a movement mechanism operatively connected to the distal end portion can be transferred from a first state to a second state radially wider than the first state, where it is radially widened in relation to the radial dimension of the rest of the probe body and of the electrode arranged at the distal end of the probe body. In this way, the electrode probe can be implanted with a thin distal end portion through an introducer sheath and vessels, whereas, at the implantation site, the distal end portion of the probe body can be radially widened in order, on the one hand, to provide sufficient perforation protection to prevent tissue perforation by the electrode and, on the other hand, to make available a large surface area for the local release of an active substance at the implantation site.

In order to anchor pacemaker electrodes securely in the epicardium, spiral-shaped or corkscrew-shaped electrodes are known which are screwed into the epicardium/myocardium by means of a device for rotation and insertion of an epicardial/myocardial electrode. The electrode is implanted with the central axis of the spiral electrode perpendicular to the surface of the myocardial tissue, which is achieved, according to DE 60 2004 005 845 T2, by means of a device for rotation and insertion of an epicardial/myocardial electrode line which contains a spiral electrode, an electrode head, an electrode body, an elongate shaft and a rotatable tube arranged rotatably via the elongate shaft, and also a distal element which comprises the electrode head and is coupled pivotably to a distal portion of the elongate shaft and to the rotatable tube, such that, by means of the pivoting of the distal element, the electrode head can be screwed into the myocardial tissue at a predefinable angle.

Using a bulky device of this kind to screw in an epicardial pacemaker electrode is unsuitable on account of the very narrow pericardial space.

SUMMARY

An object of the present invention is to make available a device for the transcutaneous or transthoracic implantation of an epicardial pacemaker electrode by means of an implantation catheter insertable into the pericardial space, which device allows the epicardial pacemaker electrode to be implanted into the epicardium/myocardium at a predefinable, suitable implantation angle, in a reproducible manner and in a stable position.

According to the invention, this object is achieved by the features as described herein.

The solution according to the invention, to make available a device for the transcutaneous implantation of an epicardial pacemaker electrode provided with a distal fixing mechanism by means of an implantation catheter insertable into the pericardial space, in which the distal end area of the electrode is connected to a shape-variable element for aligning the electrode, in particular for adjusting the implantation angle thereof, and for laterally stabilizing the electrode, permits and ensures a reproducible and stable implantation of the electrode into the epicardium/myocardium at a predefinable, suitable angle.

The guiding of the electrode end, including the distal fixing mechanism, by means of the shape-variable element ensures, on the one hand, that the electrode, during the transcutaneous insertion of the implantation catheter into the pericardial space, is aligned coaxially with respect to the implantation catheter and thereby permits a minimally invasive entry into the body tissue of a patient and, on the other hand, the shape-variable element permits safe introduction of the epicardial pacemaker electrode into the epicardium/myocardium, since the electrode tip with the fixing mechanism, through a change of shape and/or volume of the shape-variable element, is aligned at a defined angle with respect to the surface of the epicardium and can be stabilized in this alignment, thereby ensuring that the electrode is securely anchored in the epicardium/myocardium with a defined angle of entry.

The term electrode or pacemaker electrode is understood to mean a tubular, flexible probe body with an inner conductor, for example in the form of a wire coil, arranged in an insulating sleeve. The probe body has a distal end portion with an electrode tip and a fixing mechanism, and a proximal end portion with a connector, for example in the form of a plug, which is connected to a pacemaker.

In a first embodiment, the shape-variable element for adjusting the implantation angle and for laterally stabilizing the epicardial pacemaker electrode is composed of a fillable balloon, i.e. a balloon inflatable with gas or fillable with liquid, which is connected to the proximal end of the implantation catheter via a gas line or liquid line.

In this first embodiment, the empty balloon sheath is arranged in the distal end area of the implantation catheter, where the balloon sheath assumes a minimum volume such that the implantation catheter can also be configured with a minimal diameter. At the implantation site, the balloon sheath is released, for example by pulling back the outer catheter, and, when gas or liquid is supplied from the proximal end of the implantation catheter via the gas line or liquid line, can be inflated or filled to such a volume that the epicardial pacemaker electrode guided along the outer contour of the balloon is aligned at an optimal implantation angle to the epicardium/myocardium and is at the same time laterally stabilized, such that the epicardial pacemaker electrode can be securely inserted, preferably screwed, into the epicardium/myocardium.

In a preferred embodiment, the distal end of the electrode is guided in an open or closed guide channel around the balloon.

The arrangement of the electrode in an open or closed guide channel ensures that, during the insertion and in particular during the screwing-in of a spiral-shaped or corkscrew-shaped distal fixing mechanism into the epicardium/myocardium, the electrode cannot escape sideways, which would entail the danger of the optimal implantation angle not being maintained. In addition, the guide channel ensures that a spiral-shaped or corkscrew-shaped distal fixing mechanism of the electrode is screwed into the epicardium/myocardium with low friction, such that an optimal transfer of the torque takes place.

For lateral stabilization, the shape-variable element has position stabilizers protruding from the balloon and preferably arranged diametrically with respect to each other, which position stabilizers, in a preferred embodiment, are designed as part of a cross-shaped, hammer-shaped, cylinder-shaped or beam-shaped balloon.

The arrangement of position stabilizers protruding laterally from the balloon permits, on the one hand, the accommodation of the position stabilizers in the narrow pericardial space and, on the other hand, as a result of the position stabilizers bearing on the epicardium across a large surface area, a secure positioning of the epicardial pacemaker electrode at the implantation site, for the secure introduction thereof into the epicardium/myocardium.

In a second embodiment, the shape-variable element is composed of an aligning and stabilizing element, which receives the electrode and which has open or closed end-side rings and struts connecting the end-side rings, which struts, during the advance of the implantation catheter from the puncture site to the implantation site, are oriented substantially parallel to the wall of the outer catheter and, after release of the aligning and stabilizing element, deploy to an implantation position, wherein, in the implantation position, at least one central aligning strut aligns the electrode, and at least two support struts, preferably arranged on both sides of the aligning strut, stabilize the alignment and position of the electrode.

In this second embodiment of the shape-variable element, an inflatable or fillable balloon is replaced by a shape-variable aligning and stabilizing element which, for implantation, is brought forcibly into a shape in which it is aligned substantially coaxially with respect to the outer catheter, is released at the implantation site, for example by pulling back the outer catheter, and returns to a predefined curved shape which ensures both a stable position of the electrode, guided in the flexible cage, and also an alignment of the electrode at a predefined implantation angle.

Preferably, in the second embodiment of the shape-variable element, the struts of the aligning and stabilizing element that connect the end-side rings are made from a shape-memory material, in particular from nitinol, a spring material, in particular spring steel or plastic, or a pseudo-elastic material, in particular from nitinol. Alternatively, a mechanical shape-changing mechanism can also be used.

With this embodiment of the aligning and stabilizing element, use is made of the pseudo-elasticity of a shape-memory alloy in which the curved state, i.e. the state which deviates from the cylinder shape and in which the electrode guided inside the aligning and stabilizing element is brought to the optimal implantation angle, is the shape that is independently adopted. By pulling the aligning and stabilizing element into the outer catheter, the aligning and stabilizing element is brought to the shape coaxial with respect to the outer catheter and, in order to permit implantation of the electrode into the epicardium, recovers the curved original shape by means of the outer catheter being pulled back.

As an alternative to this, it is also possible to utilize the temperature-dependent shape-memory effect of nitinol, for example, in which the struts of the aligning and stabilizing element that connect the rings adopt the desired curved shape at room temperature or body temperature, whereas, during the implantation process, they are brought to a shape adapted to the outer catheter.

Alternatively, the struts of the aligning and stabilizing element that connect the end-side rings can be made from a material with elastic restoring force, which struts, in order to permit implantation, are brought to a constrained shape aligned with respect to the outer catheter and, at the implantation site, they adopt a curved shape adapted to the desired implantation angle after release, for example by means of the outer catheter being pulled back. Materials and shapes with elastic restoring force are, for example, springs, spring steel or the like.

In addition to shape-memory materials and materials and shapes with elastic restoring force, it is also possible to use polymers or materials which, under the effect of a magnetic field, adopt a desired shape in order, on the one hand, to ensure a space-saving arrangement of the shape-variable element in the outer catheter during the implantation and, on the other hand, to permit an optimal implantation angle at the implantation site, at the same time with stable positioning of the epicardial pacemaker electrode.

In a third embodiment, the shape-variable element is composed of a combination of the shape-variable elements in the first and second embodiments and has an inflatable balloon, connected to the proximal end of the implantation catheter via a gas line or liquid line, and an aligning and stabilizing element with end-side rings and flexible struts which connect the end-side rings and are made from a shape-memory material, in particular from nitinol.

In this third, combined embodiment, the balloon serves, for example, for the alignment and in particular the adjustment of the implantation angle of the electrode, while the flexible struts of the aligning and stabilizing element serve to stabilize the position of the shape-variable element at the implantation site.

The electrode is preferably arranged in a tubular, flexible inner catheter guided inside the outer catheter.

In particular, the aligning and stabilizing element is arranged between the inner catheter and the outer catheter and is connected to the distal end of the inner catheter, such that the aligning and stabilizing element, which is aligned cylindrically coaxially with respect to the outer catheter during the implantation, adopts its original or predefined and adjustable curved shape by means of the outer catheter being pulled back.

If an inner catheter is used to receive the epicardial pacemaker electrode, the proximal end of the inner catheter can thus be connected to a device for applying an underpressure in the inner catheter. The application of underpressure in the inner catheter allows the distal end of the inner catheter to be sucked onto the epicardium and thus ensures that the inner catheter is fixed to the epicardium at the implantation site, and it ensures that the adopted implantation angle is safely maintained or allows said angle to be increased. If no inner catheter is used, the distal end of the outer catheter can be sucked onto the epicardium analogously.

In the design of the shape-variable element in the first embodiment as an inflatable or Tillable balloon, the gas line or liquid line leading to the balloon can be guided in the wall of the inner catheter, between the inner catheter and the outer catheter, or along the outer face of the outer catheter.

In order to remove the inner catheter and/or outer catheter after the implantation of the epicardial pacemaker electrode in the epicardium/myocardium, a mechanism is provided for longitudinally slitting open the inner catheter and/or outer catheter during the withdrawal of the inner catheter and/or outer catheter from the body tissue. Alternatively, the lumina of outer catheter or of outer and inner catheter can be so large that they can be pulled off from the electrode.

This may be necessary if a plug connected to the electrode at the proximal end of the implantation catheter according to current industry standard IS-1 has a greater external diameter than the electrode itself, which is isodiametric as far as the electrode tip.

In all embodiments, the implantation catheter can be designed as a steerable catheter with one or two control wires at the distal end of the implantation catheter for deflecting the catheter at bends or curvatures, in order to ensure a simple advance of the implantation catheter to the implantation site.

BRIEF DESCRIPTION OF THE DRAWINGS

The underlying concept of the invention will be explained in more detail with reference to the illustrative embodiments shown in the drawing.

FIG. 4 shows a perspective view of an implantation catheter with a balloon for aligning and stabilizing the position of an epicardial pacemaker electrode, in the starting position.

FIG. 5 shows a section through the implantation catheter along the section line V-V according to FIG. 4.

FIG. 6 shows a plan view of the implantation catheter according to FIG. 4, without the balloon.

FIG. 7 shows a longitudinal section through the implantation catheter according to FIG. 4, without the balloon.

FIGS. 8 and 9 show different views of the implantation catheter with the inflated balloon for aligning and stabilizing the position of the epicardial pacemaker electrode.

DETAILED DESCRIPTION

Figure 1:
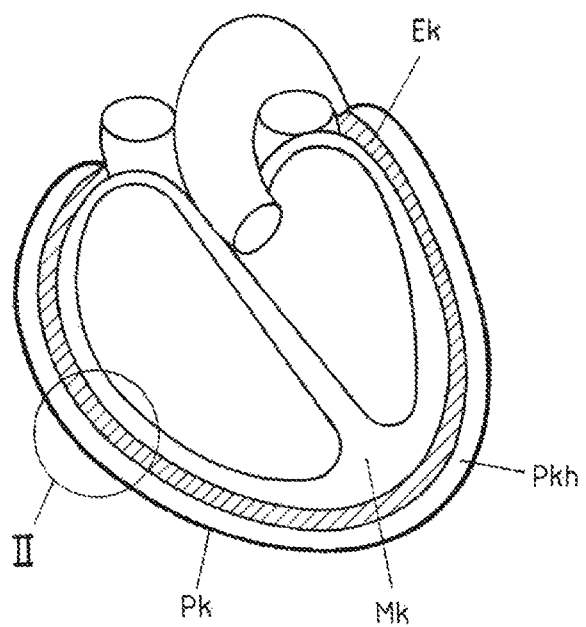
FIG. 1 shows a schematic view of a pericardium surrounding a heart.

FIG. 1 shows a schematic sectional view of a double-walled heart sac with a pericardium Pk, which forms the outer layer of the heart sac, an epicardium Ek, which forms the inner layer of the heart sac and lines the heart muscle, the myocardium Mk, and a fine space which is formed between epicardium Ek and pericardium Pk and is referred to as the pericardial cavity or pericardial space Pkh, which is filled with a liquid serving as a lubricating film.

Figure 2:
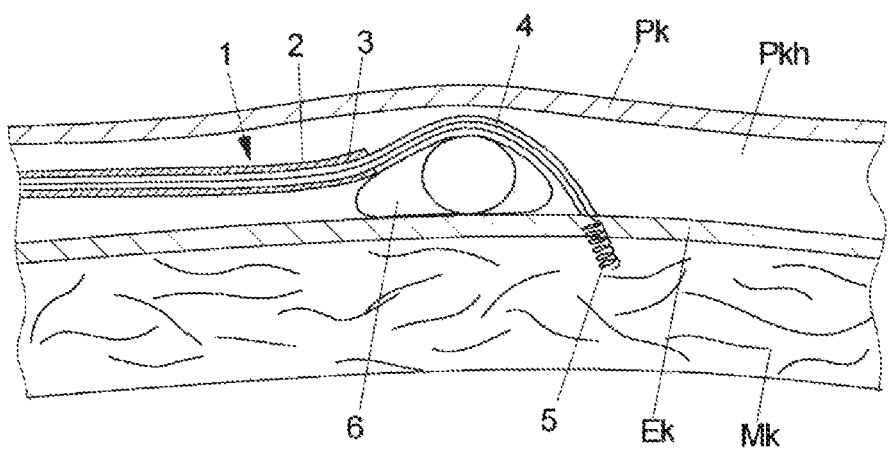
FIG. 2 shows an enlarged view of the area II of the pericardium according to FIG. 1, with an implantation catheter inserted into the pericardial space and with a balloon for aligning and stabilizing the position of an epicardial pacemaker electrode.

FIG. 2 shows an enlarged view of the area II according to FIG. 1 with the pericardium Pk, the epicardium Ek and the pericardial space Pkh formed between pericardium Pk and epicardium Ek, and also with the myocardium Mk of the heart adjacent the epicardium Ek. To implant an epicardial pacemaker electrode 4, an implantation catheter 1 is inserted, after the puncturing of the pericardium Pk, by a transcutaneous or transthoracic route into the pericardial space Pkh and is moved along the pericardial space Pkh to an implantation site that is optimal for the implantation of the epicardial pacemaker electrode 4 for myocardial excitation.

The implantation catheter 1 comprises a tubular, flexible outer catheter 2 and a tubular, flexible inner catheter 3 which is guided inside the outer catheter 2 and in which the epicardial pacemaker electrode 4 is guided, at the distal end of which a preferably screw-shaped or corkscrew-shaped fixing mechanism 5 is arranged, the latter being screwed into the epicardium/myocardium of the heart in order to permit firm anchorage in the epicardium/myocardium. For this purpose, a torque is suitably applied to the electrode 4, which is designed in such a way that the torque is transmitted to the distal end of the epicardial pacemaker electrode 4.

For optimal anchoring of the electrode 4 in the epicardium/myocardium, it is essential that the electrode 4 is screwed into the epicardium/myocardium at a suitable angle. In addition, for a satisfactory, reproducible and secure implantation of the electrode 4, it is essential that the position of the electrode 4 with respect to the pericardium is stable during the screwing-in procedure, in order, on the one hand, to maintain the optimal implantation angle and, on the other hand, to keep the lateral angle perpendicular, such that the electrode 4 is screwed into the myocardium and not parallel to the epicardium, since it then finds no hold in the epicardium/myocardium. During the screwing-in procedure, the torque applied to the electrode 4 should be transmitted optimally to the electrode 4. Therefore, when setting the implantation angle, a buckling of the inner catheter 3 has to be prevented, otherwise the friction between inner catheter 3 and electrode 4 could be increased to such an extent that it is no longer possible to screw in the electrode 4. For this purpose, the inner catheter 3 can be made, according to requirements, from variably flexible materials and/or can be equipped with a wire braid (braiding) or a wire coil (coiling).

To meet the abovementioned objects, the invention proposes a shape-variable element which, in the embodiment according to FIG. 2, is designed as a balloon 6 which, during the insertion of the implantation catheter 1 into the pericardial space Pkh, is arranged inside the outer catheter 2 and, at the implantation site, is filled with a gas or a liquid, as a result of which the volume of the balloon 6 is increased. In this way, the electrode 4 guided around the balloon 6 changes its alignment and, with respect to the epicardium/myocardium, adopts an implantation angle that is dependent on the degree of filling of the balloon 6 and thus on the change of volume of the latter.

Figure 3:
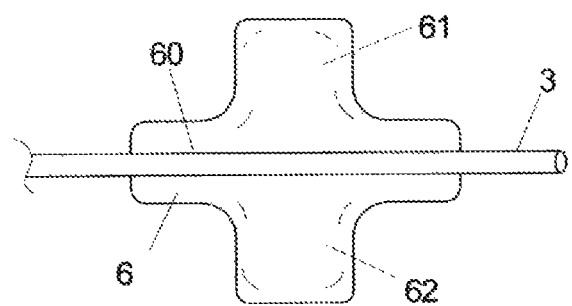
FIG. 3 shows a plan view of the balloon according to FIG. 2 with laterally deployable wings.

To stabilize the position of the balloon 6 and of the electrode 4 guided around the balloon 6 in the inner catheter 3, the balloon 6, according to the schematic plan view shown in FIG. 3, is provided, on the cross-shaped or hammer-shaped balloon 6 and on the inner catheter 3, with laterally deployable wings 61, 62 which increase the contact surface of the balloon 6 inside the pericardial space and which, during the screwing-in of the epicardial pacemaker electrode 5, prevent conjoint rotation of the balloon 6, or of the inner catheter 3 connected to the balloon 6 or guided along an open or closed guide channel 60 of the balloon 6. In particular, these lateral wings that, when an attempt is made to screw the electrode into the epicardium/myocardium, the electrode tip orients itself parallel to the surface, which would then lead to undesired slipping of the electrode tip away from the epicardium/myocardium.

FIG. 4 shows a schematic perspective view of the implantation catheter 1 in the form provided for inserting the implantation catheter 1 into the pericardial space Pkh until the implantation site is reached, and FIG. 5 shows a section through the implantation catheter 1 along the line V-V according to FIG. 4.

The implantation catheter 1 composed of an outer catheter 2 and of an inner catheter 3 guided in the lumen of the outer catheter 2 has, at the distal end of the inner catheter 3, the unfilled balloon sheath of the balloon 6. The electrode 4 is guided in the longitudinal direction in the lumen of the inner catheter 3, and a supply line 31 for filling the balloon 6 is arranged therein or is divided from the lumen for inserting the electrode 4. The supply line of the balloon 6 and the electrode 4 can also be guided in separate tubes.

FIG. 6 is a plan view and FIG. 7 a longitudinal section along the line VII-VII according to FIG. 6, both showing the implantation catheter 1 with the outer catheter 2 and the inner catheter 3 guided in the lumen of the outer catheter 2, which inner catheter 3 has a lumen 30 for insertion of the electrode 4 and a lumen serving as supply line 31 for filling the balloon 6 (not shown in FIGS. 6 and 7). An opening 32 for filling the balloon 6 is provided in the proximal end area of the inner catheter 3, while the distal end of the supply line 31 for filling the balloon 6 is closed by a wall 33. The distal end of the lumen 30 for insertion of the electrode 4 has an opening 35 through which the electrode 4 is guided. In addition, the distal opening 35 serves to suck the inner catheter 3 onto the epicardium at the implantation site, for which purpose a device for generating an underpressure is attached to the proximal end of the lumen 30 for insertion of the electrode 4.

As an alternative to an arrangement in which a lumen 31 for filling the balloon 6 is guided inside the inner catheter 3, a filling line can be guided along the outer face of the outer catheter 2 to the balloon 6 or can be arranged outside the inner catheter 3 in the lumen of the outer catheter 2. In a further alternative, the inner catheter 3 can be in the form of two separate tubes, of which one serves as balloon supply line and the other as electrode guide.

FIG. 7 shows, at the distal end of the inner catheter 3, an arch that is brought about by the filling of the balloon 6 according to FIGS. 8 and 9, wherein the balloon 6 can be filled both with a gas and with a liquid, which are fed through the lumen 31 and the opening 32 to the balloon 6.

FIGS. 8 and 9 are schematic perspective views showing the filled balloon 6 at the implantation site and illustrating the alignment of the inner catheter 3, resulting from the filling of the balloon 6, at an implantation angle dependent on the degree of filling of the balloon 6, at which implantation angle the electrode 4 is screwed into the epicardium/myocardium. To stabilize the position of the inner catheter 3 with the electrode line 4 guided therein, a guide channel 60 is provided in or on the balloon 6, in which guide channel 60 the inner catheter 3 is received or via which the inner catheter 3 is connected to the balloon 6 such that, as the epicardial pacemaker electrode 4 is screwed into the epicardium/myocardium, a change of position of the inner catheter 3 and thus of the implantation angle is avoided.

Figure 10:
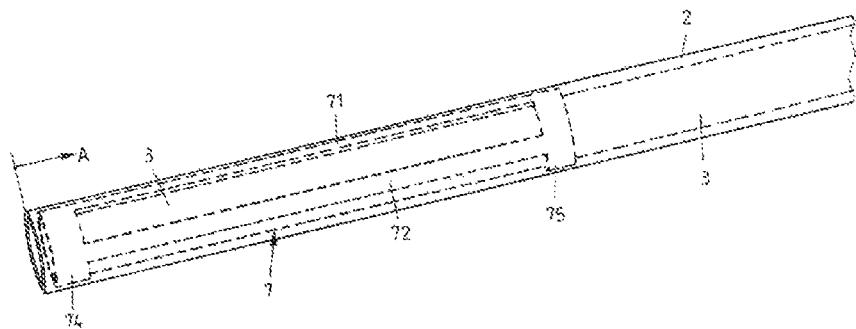
FIG. 10 shows a schematic perspective view in which an aligning and stabilizing element for aligning and stabilizing the position of an epicardial pacemaker electrode is pulled into the outer catheter.
Figure 11:
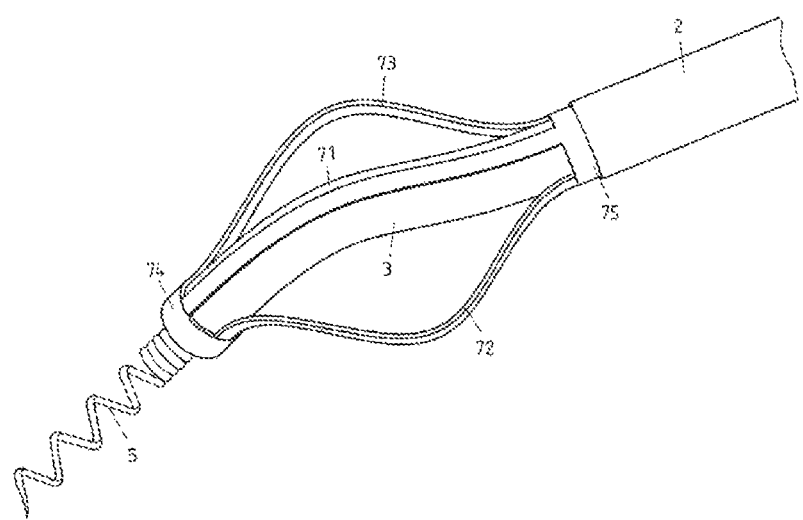
FIGS. 11 and 12 show a perspective plan view and a side view, respectively, of the shape-variable element, deployed at the implantation site, for aligning and stabilizing the position of the epicardial pacemaker electrode according to FIG. 10.
Figure 12:
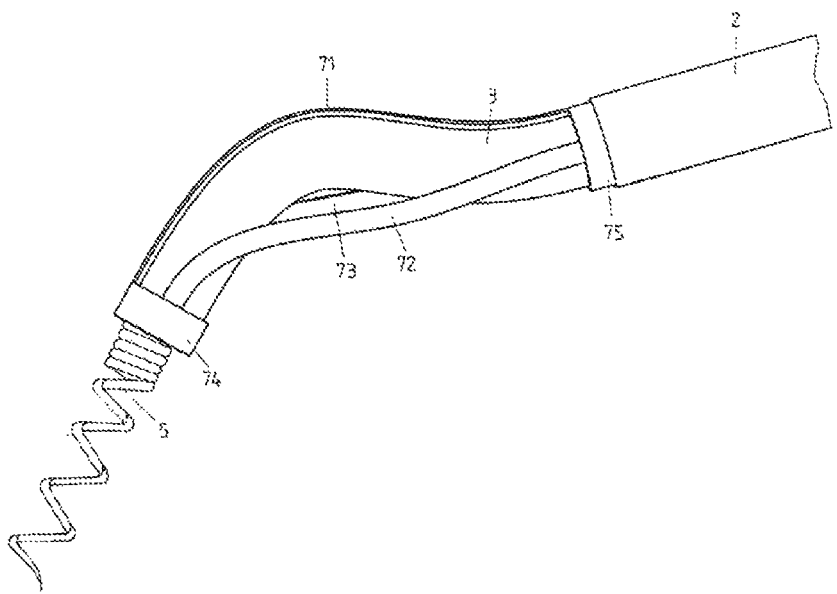

FIGS. 10 to 12 show a second illustrative embodiment of a shape-variable element for aligning or adjusting the implantation angle and for stabilizing an implantation catheter for implanting an epicardial pacemaker electrode.

According to FIG. 10, the second embodiment of a shape-variable element consists of an aligning and stabilizing element 7 (indicated by broken lines) which, in the transport state or initial state, i.e. before reaching the implantation site, is pulled into the distal end of the outer catheter 2, said aligning and stabilizing element 7 having open or closed end-side rings 74, 75 which are connected by longitudinally extending struts 71 to 73. The distal end of the inner catheter 3, in which the electrode 4 is arranged, is guided in the inside of the aligning and stabilizing element 7 guided in the outer catheter 2. The struts 71 to 73 connecting the end-side rings 74, 75 are composed of a central aligning strut 71, for adjusting the implantation angle, and two lateral support struts 72, 73, for stabilizing the position.

As an alternative to the cylinder shape of the aligning and stabilizing element 7 as shown in FIG. 10, other shapes are also possible. In particular, the aligning and stabilizing element 7 does not have to be closed all the way round in order to permit a slitting of the implantation catheter after implantation has been achieved. Moreover, the struts 71-73 do not have to be designed as straight rods; instead they can also be curved, as is also necessary in some circumstances. The numbers of the aligning struts 71 and lateral struts 72, 73 are also variable.

In FIGS. 11 and 12, the shape of the aligning and stabilizing element 7 at the implantation site is shown in two different perspective views in which, from the cylinder shape of the aligning and stabilizing element 7 as shown in FIG. 10, for example by pulling the outer catheter 2 back in the direction of the arrow A according to FIG. 10, the struts 71 to 73 adopt a shape in which the inner catheter 3 enclosed by the end-side rings 74, 75 is brought to the desired orientation for adjustment of a predefined implantation angle and, at the same time, the position of the distal end of the inner catheter 3 at the implantation site is stabilized.

The change of shape of the aligning and stabilizing element 7, from the cylinder shape shown in FIG. 10 to the aligning and stabilizing shape shown in FIGS. 11 and 12, can be achieved in different ways. Thus, the struts 71 to 73 made from a material with elastic restoring force, for example in the form of springs or spring steel, can be used, which struts adopt the extended shape shown in FIG. 10 as long as they are completely or partially enclosed by the outer catheter 2. Plastics are also conceivable. Once the implantation catheter 1 inserted into the pericardial space Pk reaches the implantation site, the constrained shape of the struts 71 to 73 is canceled by means of the outer catheter 2 being pulled back in the direction of the proximal end of the implantation catheter 1, and the struts 71 to 73 adopt a shape predefined by the elastic restoring force in accordance with FIGS. 11 and 12.

Alternatively, it is possible to utilize the pseudo-elasticity of a shape-memory material or of a shape-memory alloy, in which the curved state shown in FIGS. 11 and 12 is the shape adopted independently. By pulling the cage 7 into the outer catheter 2, the aligning and stabilizing element 7 is brought to the extended shape shown in FIG. 10. In order to align the inner catheter 3 and thus to adjust the implantation angle at the implantation site, the outer catheter 2 is pulled back in the direction of the arrow A according to FIG. 10, such that the aligning and stabilizing element 7 again independently adopts the curved shape.

The shape-memory material used for the aligning and stabilizing element 7 can be, for example, the nickel-titanium alloy nitinol, of which the temperature-dependent shape-memory effect can be utilized in an alternative embodiment of the aligning and stabilizing element 7. The alloy ratio in this case influences the transformation temperature, wherein a shape-memory material is preferably used which is composed of an alloy with a low transformation temperature of 0° C., for example, and which behaves at room temperature or body temperature like spring steel and thus adopts the desired curved shape at the implantation site. Alternatively, it is also possible to use other alloys or plastics with a shape-memory effect.

In addition to materials with a temperature-dependent shape-memory effect, it is also possible to use materials that have a shape change triggered by other effects, for example materials that can be influenced by the action of an external magnetic field.

Figure 13:
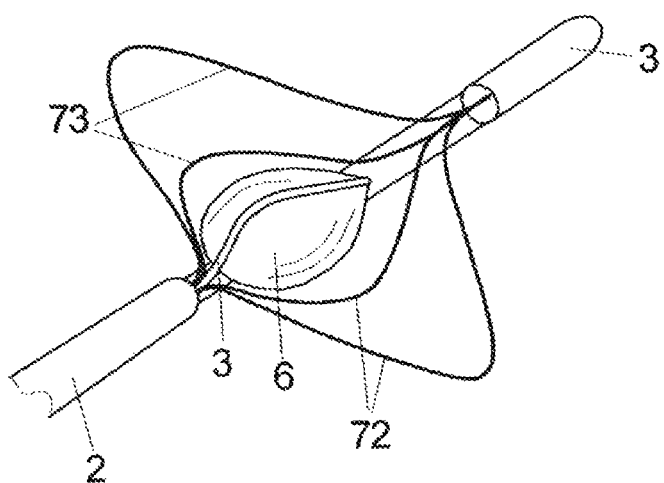
FIGS. 13 and 14 show a perspective view and a side view, respectively, of an implantation catheter with a combination of an inflatable balloon and a deployable aligning and stabilizing element for aligning and stabilizing the position of an epicardial pacemaker electrode.
Figure 14:
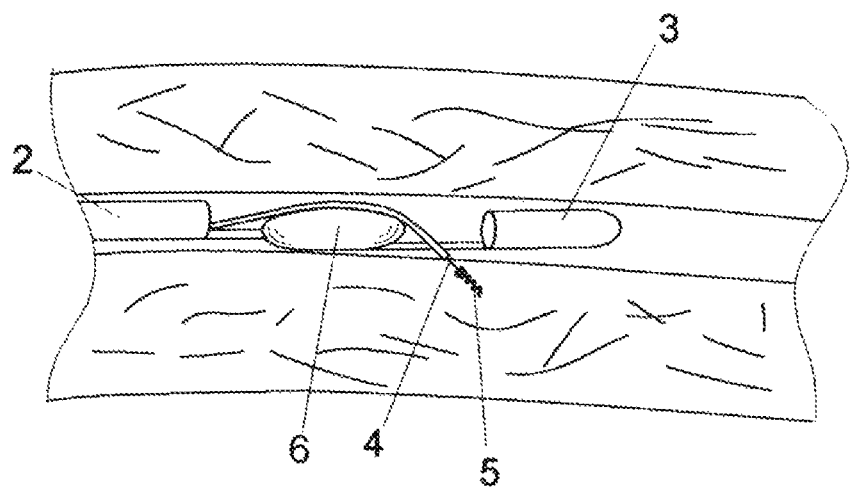

FIGS. 13 and 14 show, in a perspective plan view and in a schematic side view, a further embodiment of a shape-variable element that is composed of parts of the illustrative embodiments of a shape-variable element that have been described above with reference to FIGS. 2 to 9 and 10 to 11.

This further embodiment of a shape-variable element is composed of a balloon 6 for aligning or adjusting the implantation angle at which the epicardial pacemaker electrode 4 is screwed into the epicardium/myocardium, and of support struts 72, 73 which provide stabilization of the position and are made of nitinol, for example. Two inner catheters (inner catheter and electrode guide) are guided in the outer catheter 2. The outer catheter 2 is pulled back at the implantation site and thus frees the nitinol struts and the balloon 6. The nitinol struts, secured to the inner catheter 3, then stabilize the lateral position of the inner catheter 3 and prevent tilting. The volume of the balloon 6 is increased by filling it until the electrode guide guided in the lumen of the inner catheter 3, and thus the electrode 4 guided therein, has adopted the desired implantation angle. By pulling the outer catheter 2 back relative to the inner catheter 3, the aligning and stabilizing element 7 with the struts 72, 73 can be released beforehand, at the same time or later, such that said struts change from the extended shape to the curved shape according to FIG. 13, as a result of the shape-memory effect, and thus stabilize the position of the distal end of the implantation catheter 1.

Once the implantation of the epicardial pacemaker electrode 5 is complete, the implantation catheter with the shape-variable element 6, 7 has to be withdrawn, but this is prevented by the fact that a plug for connecting the electrode line to a pacemaker is arranged at the proximal end of the electrode line. This plug usually has a greater diameter than the implantation catheter 1, and therefore the implantation catheter 1 can no longer be easily removed after successful implantation. For this reason, the catheters are cut open lengthwise by a special knife during the withdrawal and can thus be moved past the plug.

For this purpose, the possibility of slitting open can be integrated in the implantation catheter, wherein for example the end-side rings 74, 75 of the aligning and stabilizing element 7 are not closed but instead open on one side, so as to guide the aligning and stabilizing element 7 past the special knife.

Since the implantation of the epicardial pacemaker electrode tip (helix) 5 is not effected through the vascular system to the heart but instead by a transcutaneous or transthoracic route, the implantation catheter 1 can alternatively have a larger diameter such that, with a corresponding diameter of the proximal plug that is smaller than the internal diameter of the catheter, it is possible for the implantation catheter, i.e. the outer catheter or the combination of outer catheter and inner catheter, to be pulled off from the electrode line without the catheter having to be slit open lengthwise.

LIST OF REFERENCE SIGNS 1 implantation catheter
2 outer catheter
3 inner catheter
4 epicardial pacemaker electrode
5 distal fixing mechanism (helix)
6 balloon
7 aligning and stabilizing element
30 lumen
31 gas line or liquid line
32 opening
33 wall
34 window-shaped cutout
35 opening
60 guide channel
61,62 position stabilizers (deployable balloon wings)
71 aligning strut
72, 73 position stabilizers (support struts)
74, 75 end-side rings
Ek epicardium
Mk myocardium
Pk pericardium
Pkh pericardial space

The invention claimed is:

1. A device for transcutaneous implantation of an epicardial pacemaker electrode, which is arranged in a tubular, flexible implantation catheter insertable into a pericardial space, wherein a distal end area of the electrode is connected to a shape-variable element for aligning the electrode, in particular for adjusting an implantation angle thereof, and for stabilizing, in particular laterally stabilizing, the electrode; and wherein the shape-variable element includes an aligning and stabilizing element, which receives the electrode and which has open or closed end-side rings and struts connecting the end-side rings, which struts, during advance of the implantation catheter from a puncture site to an implantation site, are disposed within an outer catheter and, after release of the aligning and stabilizing element, deploy to an implantation position.

2. The device as claimed in claim 1, wherein, in the implantation position, at least one central aligning strut aligns the electrode, and at least two support struts stabilize the alignment and position of the electrode.

3. The device as claimed in claim 1, wherein at least the struts of the aligning and stabilizing element that connect the end-side rings are made from a shape-memory material, in particular from nitinol, a spring material, in particular spring steel or plastic, or a pseudo-elastic material, in particular from nitinol.

4. The device as claimed in claim 1, wherein at least the struts of the aligning and stabilizing element that connect the end-side rings are made from a material with elastic restoring force.

5. The device as claimed in claim 1, wherein the electrode is arranged in a tubular, flexible inner catheter of the implantation catheter guided inside an outer catheter.

6. The device as claimed in claim 5, wherein an aligning and stabilizing element is arranged between the inner catheter and the outer catheter and is connected to the distal end of the inner catheter.

7. The device as claimed in claim 5, wherein the proximal end of the implantation catheter is connected to a device for sucking the distal end of the implantation catheter onto the epicardium.

8. The device as claimed in claim 5, wherein the open or closed end-side rings are open on at least one side and are configured to guide the aligning and stabilizing element past a mechanism for longitudinally slitting open the inner catheter and/or outer catheter.

9. The device as claimed in claim 1, wherein the shape-variable element arranged at the distal end of the electrode includes an inflatable balloon, which is connected via a supply line to the proximal end of the implantation catheter.

* * * * *